United States Patent [19]
Bunting et al.

[11] Patent Number: 5,935,924
[45] Date of Patent: *Aug. 10, 1999

[54] TREATMENT OF CONGESTIVE HEART FAILURE

[75] Inventors: Stuart Bunting, Montara; Ross Clark, Pacifica; Nancy Gillett, El Granada; Hongkui Jin, Los Altos; Renhui Yang, San Bruno, all of Calif.

[73] Assignee: Genentech, Inc., South San Francisco, Calif.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/228,548

[22] Filed: Apr. 15, 1994

[51] Int. Cl.$^6$ ..................................................... A61K 38/00
[52] U.S. Cl. ............................................... 514/2; 514/423
[58] Field of Search ........................................ 514/2, 423

[56] References Cited

U.S. PATENT DOCUMENTS 5,370,870  12/1994  Wong .

FOREIGN PATENT DOCUMENTS

WO 9207578  5/1992  WIPO .
WO 9211865  7/1992  WIPO .
WO 9222311  12/1992  WIPO .

OTHER PUBLICATIONS

Yang et al., "Effects of Growth Hormone in Rats with Postinfarction Left Ventricular Dysfunction" *Cardiovascular Drugs and Therapy* 9:125–131 (1995).
Amato et al., "Body Composition, Bone Metabolism, and Heart Structure and Function in Growth Hormone (GH)–Deficient Adults before and after GH Replacement Therapy at Low Doses", *J. Clin. Endocrinol Metab.*, 77:1671–76 (1993).
Ambler et al., "Improvement of doxorubicin induced cardiomyopathy in rats treated with insulin–like growth factor I", *Cardiovascular Research*, 27:1368–1373 (1993).
Buttrick et al., Effects of chronic dobutamine on cardiac mechanics and biochemistry after myocardial infarction in rats, *Am. J. Physiol* 260:11473–11479 (1991).
Caidahl et al., "Cardiovascular and renal effects of growth hormone", *Clinical Endocrinology* 40:393–400 (1994).
The Captopril–Digoxin Multicenter Research Group, "Comparative Effects of Therapy With Captopril and Digoxin in Patients With Mild to Moderate Heart Failure", *JAMA* 259(4):539–544 (1988).
Captopril Multicenter Research Group, "A Placebo–Controlled Trial of Captopril in Refractory Chronic Congestive Heart Failure", *JACC* 2(4):755–763 (1983).
Castagnino et al., "Bivalent Effects of Human Growth Hormone in Experimental Myocardial Infarcts; Protective When Administered Alone and Aggravating When Combined with Beta Blockers", 31:845–855 (1990).
Castagnino et al., "Preservation of the myocardial collagen framework by human growth hormone in experimental infarctions and reduction in the incidence of ventricular aneurysms", *Int. J. Cardiol.* 35:101–114 (1992).
Celniker et al., "Variability in the Quantitation of Circulating Growth Hormone Using Commercial Immunoassays", *J.Endocrinology/Metabolism* 68:469–476 (1989).
Christiansen et al., "Beneficial effects of GH replacement therapy in adults", *Acta Endocrinol.* 125:7–13 (1991).
Clemmons et al., "Reversal of Diet–Induced Catabolism by Infusion of Recombinant Insulin–Like Growth Factor–I in Humans", *J. Clin Endocrinol* 75:234–238 (1992).
Cohn et al., "A Comparison of Enalapril with Hydralazine–Isosorbide Dinitrate in the Treatment of Chronic Congestive Heart Failure", *The New England Journal of Medicine,* 325(5):303–310 (1991).
The Consensus Trial Study Group, "Effects of Enalapril on Mortality in Severe Congestive Heart Failure", *The New England Journal of Medicine* 316 (23):1429–1435 (1987).
Csanady et al., "The heart in acromegaly: an echocardiographic study", *Int. J. Cardiol* 2:349–361 (1983).
Fazio et al., "Evidence for biventricular involvement in acromegaly: a Doppler echocardiographic study", *Eur Heart J.* 14:26–33 (1993).
Florini, "Hormonal Control of Muscle Growth", *Muscle & Nerve* 10:577–598 (1987).
Froesch et al., "Therapeutic Potential of Insulinlike Growth Factor I", *Trends in Endocrinology/Metabolism* 1(5):254–260 (1990).
Furlanetto et al., "Estimation of Somatomedin–C Levels in Normals and Patients with Pituitary Disease by Radioimmunoassay", *The Journal of Clinical Investigation* 60:648–657 (1977).
Geenen et al., "Papillary mechanics and cardiac morphology of infarcted rat hearts after training", *J. Appl. Physical,* 63:92–96 (1987).
Guler et al., "Short–Term Metabolic Effects of Recombinant Human Insulin–Like Growth Factor I in Healthy Adults", *The New England Journal of Medicine* 317(3):137–140 (1987).

(List continued on next page.)

*Primary Examiner*—Keith D. MacMillan
*Attorney, Agent, or Firm*—Janet E. Hasak

[57] ABSTRACT

A mammal with congestive heart failure is treated by administering to the mammal an effective amount of growth hormone. Treatment results in increased left ventricular cystolic pressure, increased left ventricular maximum, increased cardiac output, and increased stroke volume index. Treatment also results in reduced left ventricular end-diastolic pressure and reduced systemic vascular resistance. These measurements indicate improvement in cardiac function by increased ventricular contractility and decreased peripheral vascular resistance.

12 Claims, 5 Drawing Sheets

OTHER PUBLICATIONS

Kahaly et al., "Arrhythmia profile in acromegaly", *Eur Heart J.* 13:51–56 (1992).

Kloner et al., "The effect of early exercise on myocardial infarct scar formation", *Amer. Heart Journal* 106(5):1009–1013 (1983).

Kramer et al., "Controlled Trial of Captopril in Chronic Heart Failure: A Rest and Exercise Hemodynamic Study", *Circulation* 67(4):807–816 (1983).

Kupfer et al., "Enhancement of the Anabolic Effects of Growth Hormone and Insulin–Like Growth Factor I by Use of Both Agents Simultaneously", *Amer. Soc. for Clin. Invest.* 91:391–396 (1983).

Lei et al., "Cardiac Architectural Changes with Hypertrophy Induced by Excess Growth Hormone in Rats", *Lab Invest.,* 59:357–362 (1988).

Lim et al., "Rapid Reduction of Left Ventricular Hypertrophy in Acromegaly after Suppression of Growth Hormone Hypersecretion", *Ann Intern Med.,* 117:719–726 (1992).

Merola et al., "Cardiac Structural and Functional Abnormalities in Adult Patients with Growth Hormone Deficiency", *J. Clin. Endocrinol Metab* 77:1658–1661 (1993).

Metcalfe et al., "Metabolic Effects of Acute and Prolonged Growth Hormone Excess in Normal and Insulin–deficient Man", *Diabetologia* 20:123–128 (1981).

Pollock et al., "Usefulness of Bucindolol in Congestive Heart Failure", *Am J Cardiol* 66:603–607 (1990).

Shahi et al., "Myocardial dysfunction in treated adult hypopituitarism: a possible explanation for increased cardiovascular mortality", *Br Heart J* 67:92–96 (1992).

Sherwin et al., "Effect of Growth Hormone on Oral Glucose Tolerance and Circulating Metabolic Fuels in Man", *Diabetologia* 24:155–161 (1983).

Sicolo et al., "Acromegalic cardiopathy: A left ventricular scintigraphic study", *J. Endocrinol. Invest.* 16:123–127 (1993).

The SOLVD Investigators, "Effect of Enalapril on Survival in Patients with Reduced Left Ventricular Ejection Fractions and Congestive Heart Failure", *The New England Journal of Medicine* 325(5):293–302 (1991).

Takano et al., "Effects of sc Administration of Recombinant Human Insulin–Like Growth Factor I (IGF–I) on Normal Human Subjects", *Endocrinol. Japon.* 37(2):309–317 (1990).

Vetter et al., "Insulin–like growth factors and insulin increase the contractility of neonatal rat cardiocytes in vitro", *Basic Res. Cardiol* 83:647–654 (1988).

Yang, R. et al., "J. Heart Failure", *Abstract Suppl* 1:793 (1993).

Banskota et al., "Characterization of Induction of Protooncogene c–myc and Cellular Growth in Human Vascular Smooth Muscle Cells by Insulin and IGF–I" *Diabetes* 38:123–129 (1989).

Beznak, "The Restoration of Cardiac Hypertrophy and Blood Pressure in Hypophysectomized Rats by Large Doses of Lyophilized Anterior Pituitary and Growth Hormone" *J. Physiol. (Lond.)* 124:64–74 (1954).

Boulware et al., "Diverse Effects of Insulin–like Growth Factor I on Glucose, Lipid, and Amino Acid Metabolism" *Am. J. Physiol.* 262:E130–E133 (1992).

Bugaisky et al., "Cellular and Molecular Mechanisms of Cardiac Hypertrophy" *The Heart and Cardiovascular System* 2:1621–1640 (1992).

Caidahl et al., "Cardiovascular and Renal Effects of Growth Hormone" *Acta Endocrinologica* 128(Suppl. 2):68 (1993).

Chanson et al., "Cardiovascular Effects of the Somatostatin Analog Octreotide in Acromegaly" *Annals Int. Med.* 113:921–925 (1990).

Cittadini et al., "Impaired Cardiac Performance in GH–Deficient Adults and its Improvement after GH Replacement" *Am. J. Physiol.* 267:E219–E225 (1994).

Cuneo et al., "Cardiac Failure Responding to Growth Hormone" *Lancet* pp. 838–839 (1989).

Cuneo et al., "Cardiovascular effects of growth hormone treatment in growth–hormone–deficient adults: stimulation of the renin–aldosterone system" *Clinical Science* 81:587–592 (1991).

Cuneo et al., "Growth Hormone Treatment Improves Serum Lipids and Lipoproteins in Adults with Growth Hormone Deficiency" *Metabolism* 42(12):1519–1523 (Dec. 1993).

Donohue et al., "Evidence that Antihypertensive Agents Lessen Ventricular Hypertrophy by Inhibiting Cardiac Expression of Insulin–like Growth Factor–I" *J. Am. Coll. Cardiol.* 19:85A (Mar. 1992).

Donohue et al., "Induction of Myocardial Insulin–like Growth Factor–I Gene Expression in Left Ventricular Hypertrophy" *Circulation* 89(2):799–809 (1994).

Flyvbjerg et al., "Inhibitory Effect of Octreotide on Growth Hormone–Induced IGF–I Generation and Organ Growth in Hypophysectomized Rats" *Am. J. Physiol.* 260:E568–E574 (1991).

Friberg et al., "Right but not Left Ventricular Insuline–Like Growth Factor 1 (IGF–1) and Growth Hormone (GH)–Receptor Levels Increase After Induction of Volume Overload" *Hypertension* 22(3):418 (A65) (Sep. 1993).

Frustaci et al., "Reversible Dilated Cardiomyopathy Due to Growth Hormone Deficiency" *Am. J. Clin. Pathol.* 97:503–511 (1992).

Gilbert et al., "Cardiac Morphology in Rats with Growth Hormone–producing Tumours" *J. Mol Cell Cardiol* 17:805–811 (1985).

Guler et al., "Recombinant human insulin–like growth factor I stimulates growth and has distinct effects on organ size in hypophysectomized rats" *Proc. Natl. Acad. Sci. USA* 85:4889–4893 (1988).

Guse et al., "Identification and Characterization of Insulin–like Growth Factor Receptors on Adult Rat Cardiac Myocytes: Linkage to Inositol 1,4,5–Trisphosphate Formation" *Endocrinology* 130(1):145–151 (1992).

Hanson et al., "Induction of Cardiac Insulin–Like Growth Factor I Gene Expression in Pressure Overload Hypertrophy" *Am. J. Med. Sci.* 306:69–74 (1993).

Hayward et al., "Acromegalic Heart Disease: Influence of Treatment of the Acromegaly on the Heart" *Otr J of Med.* 62(237):41–58 (1987).

Hirsch et al., "Cardiac Function in Acromegaly" *Am. J. Med. Sciences* 257:1–8 (1969).

Hjalmarson et al., "Effects of Growth Hormone and Insulin on Amino Acid Transport in Perfused Rat Heart" *Am. J. Physiol.* 217(6):1795–1802 (1969).

Isgaard et al., "Growth Hormone Regulates the Level of Insulin–like Growth Factor–I mRNA in Rat Skeletal Muscle" *J. Endocrinol.* 120:107–112 (1989).

Ito et al., "Insulinlike Growth Factor–I Induces Hypertrophy With Enhanced Expression of Muscle Specific Genes in Cultured Rat Cardiomyocytes" *Circulation* 87:1715–1721 (1993).

Jorgensen et al., "Long–term Growth Hormone Treatment in Growth Hormone Deficient Adults" *Acta Endocrinologica* 125:449–453 (1991).

Kahaly et al., "Relation of endocrine and cardiac findings in acromegalics" *J Endocrinol Invest.* 15:13–18 (1992).

Korner, "Anabolic Action of Growth Hormone" *Ann. N.Y. Acad. Sci.* 148:408–418 (1968).

Kostyo and Nutting, "Growth Hormone and Protein Metabolism" *Handbook of Physiology*, Greep et al., Washington, DC:American Physiological Society vol. IV, part 2(Sect. 7):187–210 (1974).

LaFranchi et al., "Effect of Growth Hormone Replacement on Development of Hypothyroidism and Hyperlipidemia" *J. Pediatrics* 106:588–593 (1985).

Lie et al., "Pathology of the heart in acromegaly: anatomic findings in 27 autopsied patients" *Amer Heart J.* 100:41–52 (1980).

Luboshitzki et al., "The Heart in Acromegaly: Correlation of Echocardiographic and Clinical Findings" *Isr. J Med Sci.* 16:378–383 (1980).

Martins et al., "Cardiac Size and Function in Acromegaly" *Circulation* 56:863–869 (1977).

Mather et al., "Heart size and function in acromegaly" *British Heart Journal* 41:697–701 (1979).

Mathews et al., "Regulation of Rat Growth Hormone Receptor Gene Expression" *Journal of Biological Chemistry* 264:9905–9910 (1989).

McGuffin et al., "Acromegaly and Cardiovascular Disorders" *Annals of Internal Medicine* 81:11–18 (1974).

Prysor–Jones and Jenkins, "Effect of Excessive Secretion of Growth Hormone on Tissues of the Rat, with Particular Reference to the Heart and Skeletal Muscle" *J. Endocr.* 85:75–82 (1980).

Rodrigues et al., "Subclinical cardiac dysfunction in acromegaly: evidence for a specific disease of heart muscle" *Br Heart J* 62:185–194 (1989).

Rosen and Bengtsson, "Premature Mortality Due to Cardiovascular Disease in Hypopituitarism" *Lancet* 336:285–288 (1990).

Rosen et al., "Cardiovascular Risk Factors in Adult Patients with Growth Hormone Deficiency" *Acta Endocrinologica* 129:195–200 (1993).

Sacca et al., "Growth Hormone and the Heart" *Endocrine Reviews* 15(5):555–573 (1994).

Savage et al., "Echocardiographic Assessment of Cardiac Anatomy and Function in Acromegalic Patients" *The Amer. J of Med.* 67:823–829 (1979).

Sklar et al., "Developmental Expression of the Tissue Insulin–like Growth Factor II/Mannose 6–Phosphate Receptor in the Rat" *Journal of Biological Chemistry* 264(28):16733–16738 (1989).

Smallridge et al., "Acromegaly and the Heart" *The Amer. J of Med.* 66:22–27 (1979).

Wahlander et al., "Left Ventricular Insulin–like Growth Factor I Increases in Early Renal Hypertension" *Hypertension* 19:25–32 (1992).

Xu and Best, "Decreased transient outward K+ current in ventricular myocytes from acromegalic rats" *Am J. Physiol* 260:H935–H942 (1991).

Yang, "Cardiac Effects of Growth Hormone in a Rat Model of Congestive Heart Failure" *Clinical Research* 42(2):325A (1994).

Christiansen et al., "Cardiovascular effects of growth hormone—with special reference to growth hormone replacement therapy", *Acta Paediatr Suppl* 383:40–42 (1992).

Cuneo et al., "Growth hormone treatment in growth hormone–deficient adults. II. Effects on exercise performance" *Amer. Physiological Soc.* 2:695–700 (1991).

Jorgensen et al., "Beneficial Effects of Growth Hormone Treatment in GH–Deficient Adults", *The Lancet* pp. 1221–1224 (1989).

Mayoux et al., "Mechanical Properties of Rat Cardiac Skinned Fibers Are Altered by Chronic Growth Hormone Hypersecretion", *Circulation Research* 72(1):57–64 (1989).

Penney et al., "Cardiomegaly and haemodynamics in rats with a transplantable growth hormone–secreting tumour", *Cardiovasculr Research* 19:270–277 (1985).

Rubin et al., "Cardiac Physiology, Biochemistry and Morphology in Response to Excess Growth Hormone in the Rat", *J. Mol. Cell Cardiol* 22:429–438 (1990).

Thuesen et al., "Increased myocardial contractility following growth hormone administration in normal man", *Dan Med Bull* 35:193–196 (1988).

Timsit et al., "Effects of Chronic Growth Hormone Hypersecretion on Intrinsic Contractility, Energetics, Isomyosin Pattern, and Myosin Adenosine Triphosphatase Activity of Rat Left Ventricle", *Amer. Soc. for Clin. Invest.* 86:507–515 (1990).

Timsit et al., "Effects of chronic growth hormone excess on cardiac contractility and myosin phenotype in the rat", *Acta Paediatr Suppl.* 383:32–34 (1992).

Yang et al., "Growth Hormone Improves Heart Function in Rats with Congestive Heart Failure", *The Journal of Heart Failure* 1(Ab. Suppl.):793 (1993).

TREATMENT OF CONGESTIVE HEART FAILURE

BACKGROUND OF THE INVENTION

1. Field of the Invention

This invention relates to the field of treating patients having congestive heart failure with growth hormone (GH).

2. Description of Background and Related Art

In vitro studies have shown that chronic hypersecretion of growth hormone by implantation of a growth hormone-secreting tumor is associated with an increase in the maximum isometric force of left ventricular papillary muscle normalized per cross-sectional area and no change in both the unloaded shortening velocity of the isolated muscle and the calcium and actin-activated myosin in normal rats. This is observed despite a marked shift of the isomyosin pattern toward the low ATPase activity V3 isoform. These results suggest that growth hormone may induce a unique pattern of myocardial contraction: a normal shortening speed and an increased force generation are associated with changes in myosin phenotype that allow the cardiac muscle to function more economically. Timsit, J. et al., *J. Clin. Invest.* 86:507–515 (1990); Timsit, J. et al., *Acta Paediatr Suppl* 383:32–34 (1992).

In vitro studies from the same investigators were carried out on rat cardiac skinned fibers. These studies have demonstrated that the contractile performance of the skinned fiber from rat myocardium subjected to chronically high circulating growth hormone levels is increased. The increase in contractile performance was shown to be due to specific alterations in the properties of the contractile apparatus, including an increase in both maximal tension and myofibrillar sensitivity to calcium. Mayoux, E. et al., *Circulation Research* 72(1):57–64 (1993).

It has been found that left ventricular dP/dt, cardiac index, stroke index, and stroke work are significantly increased in chloralose-urethan-anesthetized rats with a transplantable growth hormone-secreting tumor. The data suggest that chronic hypersecretion of growth hormone increases cardiac output by increasing contractility in anesthetized rats. Penney, D. G. et al., *Cardiovascular Research* 19:270–277 (1985).

A contrary result has also been reported. Rubin, S. A. et al., *J. Mol. Cell Cardiol.* 22:429–438 (1990) have reported that similar chronic hypersecretion of growth hormone induced by the growth hormone-secreting tumor causes significant decreases in left ventricular contractility (maximum dP/dt) and increases in LVEDP in ketamine-anesthetized rats.

In a clinical study, it has been shown that administration of human growth hormone to normal subjects for one week increases ventricular contractility and cardiac output, as evaluated by echocardiography. Thuesen, L. et al., *Dan. Med. Bull.* 35:193–196 (1988).

In adults with growth hormone deficiency, growth hormone treatment produced significant increases in stroke volume and exercise capacity. These results suggest that growth hormone can improve cardiac function at rest and during exercise in the adult patients with growth hormone deficiency. Jorgensen, J. et al., *Lancet* i:1221–1225 (1989); Cuneo, R. et al., *J. Appl. Physiol.* 70:695–700 (1991); Christiansen, J. S. et al., *Acta Paediatr Suppl* 383:40–42 (1992).

Cuneo et al., *Lancet* i:838–839 (1989) have reported a very interesting case showing effects of growth hormone therapy in a patient with extremely poor cardiac function. The patient developed severe heart failure eight months after hypophysectomy for Cushing syndrome. Standard therapy including diuretics and angiotensin-converting enzyme inhibitors had little effect and cardiac transplantation was considered. As a last resort, treatment with human growth hormone, 12 IU/day s.c. was tried, with a remarkable beneficial effect. Clinical improvement and increases in myocardial contractility and cardiac output were noted.

Until now, however, effects of human growth hormone in heart failure patients without growth hormone deficiency have not been reported, to applicants' knowledge. Heart failure affects approximately three million Americans, developing in about 400,000 each year. Current therapy for heart failure is insufficient. Although angiotensin converting enzyme (ACE) inhibitors have been shown to have beneficial effects in patients with heart failure, they appear consistently unable to relieve symptoms in more than 60% of heart failure patients. In addition, they reduce mortality of heart failure only by approximately 15–20%. Therefore, there is room for improvement in the therapy of heart failure.

Accordingly it is an object of this invention to provide a method of treatment for a patient with congestive heart failure.

SUMMARY

The present invention achieves this object by the provision of a method of treatment of congestive heart failure, the method characterized by administration of an effective amount of growth hormone (GH). The administration of GH results in improvement of cardiac function by increased ventricular contractility and decreased peripheral vascular resistance.

Figure 1A:
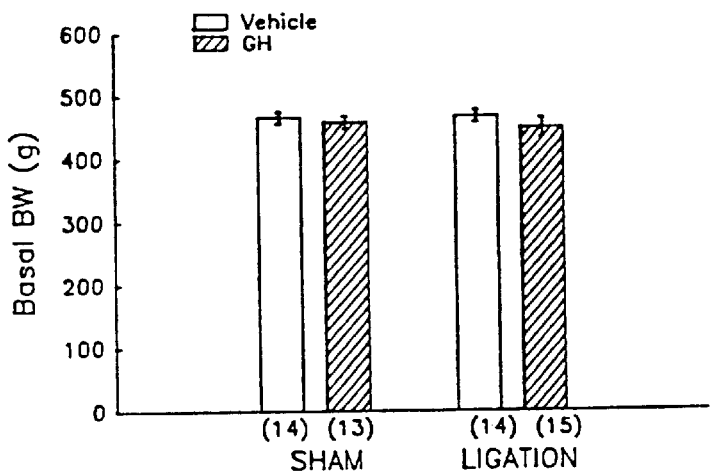
FIG. 1a. Shows the body weight before treatment in ligated and sham controls. **$P<0.01$, compared to the respective vehicle group.

DETAILED DESCRIPTION OF THE INVENTION a. Definitions

In general, the following words or phrases or abbreviations have the indicated definition when used in the description, examples, and claims:

As used herein, "BW" refers to body weight.

As used herein, "CO" refers to cardiac output.

As used herein, "CI" refers to cardiac index. The cardiac index is measurable as cardiac output divided by body weight (CO/BW).

As used herein, "dP/dt" refers to left ventricular maximum.

As used herein, "HR" refers to heart rate.

As used herein, "LCA" refers to left coronary artery.

As used herein, "LVEDP" refers to left ventricular end-diastolic pressure.

As used herein, "LVMP" refers to left ventricular mean pressure.

As used herein, "LVSP" refers to left ventricular systolic pressure.

As used herein, "MAP" refers to mean arterial pressure.

As used herein, "RAP" refers to right atrial pressure.

As used herein, "SAP" refers to systolic arteriol pressure.

As used herein, "SV" refers to stroke volume. The stroke volume is measurable as CO/HR.

As used herein, "SVI" refers to stroke volume index. The stroke volume index is measurable as SV/BW.

As used herein, "SVR" refers to systemic vascular resistance. The SVR is measurable as MAP/CI.

As used herein, "VW" refers to ventricular weight.

As used herein "infarct" refers to an area of necrosis resulting from an insufficiency of blood supply. "Myocardial infarction" refers to myocardial necrosis resulting from the insufficiency of coronary blood supply.

As used herein "treatment" refers to ameliorating the congestive heart failure condition.

As used herein, the term "mammal" refers to any animal classified as a mammal, including humans, domestic and farm animals, and zoo, sports, or pet animals, such as dogs, horses, cats, cows, etc. Preferably, the mammal herein is human.

As used herein, "growth hormone" or "GH" refers to growth hormone in native-sequence or in variant form, and from any source, whether natural, synthetic, or recombinant. Examples include human growth hormone (hGH), which is natural or recombinant GH with the human native sequence (somatotropin or somatropin), and recombinant growth hormone (rGH), which refers to any GH or variant produced by means of recombinant DNA technology, including somatrem, somatotropin, and somatropin. Preferred herein for human use is recombinant human native-sequence, mature GH with or without a methionine at its N-terminus. More preferred is methionyl human growth hormone (met-hGH) produced in E. coli, e.g., by the process described in U.S. Pat. No. 4,755,465 issued Jul. 5, 1988 and Goeddel et al., Nature, 282:544 (1979). Met-hGH, which is sold under the trademark Protropin® by Genentech, Inc., is identical to the natural polypeptide, with the exception of the presence of an N-terminal methionine residue. This added amino acid is a result of the bacterial protein synthesis process. Also preferred is recombinant hGH available from Genentech, Inc. under the trademark Nutropin®. This latter hGH lacks this methionine residue and has an amino acid sequence identical to that of the natural hormone. See Gray et al., Biotechnology, 2:161 (1984). Both methionyl hGH and hGH have equivalent potencies and pharmacokinetic values. Moore et al., Endocrinology, 122:2920–2926 (1988). Another appropriate hGH candidate is an hGH variant that is a placental form of GH with pure somatogenic and no lactogenic activity as described in U.S. Pat. No. 4,670,393 issued Jun. 2, 1987. Also included are GH variants as described in WO 90/04788 published May 3, 1990 and WO 92/09690 published Jun. 11, 1992.

b. Modes for Carrying Out the Invention

Therapeutic Compositions and Administration of GH

Therapeutic formulations of GH are prepared for storage by mixing GH having the desired degree of purity with optional physiologically acceptable carriers, excipients, or stabilizers (Remington's Pharmaceutical Sciences, supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

For administration, GH may be complexed or bound to a polymer to increase its circulatory half-life. Examples of polyethylene polyols and polyoxyethylene polyols useful for this purpose include polyoxyethylene glycerol, polyethylene glycol, polyoxyethylene sorbitol, polyoxyethylene glucose, or the like. The glycerol backbone of polyoxyethylene glycerol is the same backbone occurring in, for example, animals and humans in mono-, di-, and triglycerides.

The polymer need not have any particular molecular weight, but it is preferred that the molecular weight be between about 3500 and 100,000, more preferably between 5000 and 40,000. Preferably the PEG homopolymer is unsubstituted, but it may also be substituted at one end with an alkyl group. Preferably, the alkyl group is a C1–C4 alkyl group, and most preferably a methyl group. Most preferably, the polymer is an unsubstituted homopolymer of PEG, a monomethyl-substituted homopolymer of PEG (mPEG), or polyoxyethylene glycerol (POG) and has a molecular weight of about 5000 to 40,000.

The GH is covalently bonded via one or more of the amino acid residues of the GH to a terminal reactive group on the polymer, depending mainly on the reaction conditions, the molecular weight of the polymer, etc. The polymer with the reactive group(s) is designated herein as activated polymer. The reactive group selectively reacts with free amino or other reactive groups on the GH. It will be understood, however, that the type and amount of the reactive group chosen, as well as the type of polymer employed, to obtain optimum results, will depend on the particular GH employed to avoid having the reactive group react with too many particularly active groups on the GH. As this may not be possible to avoid completely, it is recommended that generally from about 0.1 to 1000 moles, preferably 2 to 200 moles, of activated polymer per mole of protein, depending on protein concentration, is employed. The final amount of activated polymer per mole of protein is a balance to maintain optimum activity, while at the same time optimizing, if possible, the circulatory half-life of the protein.

While the residues may be any reactive amino acids on the protein, such as one or two cysteines or the N-terminal amino acid group, preferably the reactive amino acid is lysine, which is linked to the reactive group of the activated polymer through its free epsilon-amino group, or glutamic or aspartic acid, which is linked to the polymer through an amide bond.

The covalent modification reaction may take place by any appropriate method generally used for reacting biologically active materials with inert polymers, preferably at about pH 5–9, more preferably 7–9 if the reactive groups on the GH are lysine groups. Generally, the process involves preparing an activated polymer (with at least one terminal hydroxyl group), preparing an active substrate from this polymer, and thereafter reacting the GH with the active substrate to produce the GH suitable for formulation. The above modification reaction can be performed by several methods, which may involve one or more steps. Examples of modifying agents that can be used to produce the activated polymer in a one-step reaction include cyanuric acid chloride (2,4,6-trichloro-S-triazine) and cyanuric acid fluoride.

In one embodiment the modification reaction takes place in two steps wherein the polymer is reacted first with an acid anhydride such as succinic or glutaric anhydride to form a carboxylic acid, and the carboxylic acid is then reacted with a compound capable of reacting with the carboxylic acid to form an activated polymer with a reactive ester group that is capable of reacting with the GH. Examples of such compounds include N-hydroxysuccinimide, 4-hydroxy-3-nitrobenzene sulfonic acid, and the like, and preferably N-hydroxysuccinimide or 4-hydroxy-3-nitrobenzene sulfonic acid is used. For example, monomethyl substituted PEG may be reacted at elevated temperatures, preferably about 100–110° C. for four hours, with glutaric anhydride. The monomethyl PEG-glutaric acid thus produced is then reacted with N-hydroxysuccinimide in the presence of a carbodiimide reagent such as dicyclohexyl or isopropyl carbodiimide to produce the activated polymer, methoxy-polyethylene glycolyl-N-succinimidyl glutarate, which can then be reacted with the GH. This method is described in detail in Abuchowski et al., *Cancer Biochem. Biophys.* 7:175–186 (1984). In another example, the monomethyl substituted PEG may be reacted with glutaric anhydride followed by reaction with 4-hydroxy-3-nitrobenzene sulfonic acid (HNSA) in the presence of dicyclohexyl carbodiimide to produce the activated polymer. HNSA is described by Bhatnagar et al., *Peptides: Synthesis-Structure-Function, Proceedings of the Seventh American Peptide Symposium*, Rich et al. (eds.) (Pierce Chemical Co., Rockford Ill., 1981), p. 97–100, and in Nitecki et al., *High-Technology Route to Virus Vaccines* (American Society for Microbiology: 1986) entitled "Novel Agent for Coupling Synthetic Peptides to Carriers and Its Applications."

Specific methods of producing GH conjugated to PEG include the methods described in U.S. Pat. No. 4,179,337 on PEG-GH and U.S. Pat. No. 4,935,465, which discloses PEG reversibly but covalently linked to GH. Other specific methods for producing PEG-GH include the following:

PEGylation with methoxypolyethylene glycol aldehyde (Me-PEG aldehyde) by reductive alkylation and purification is accomplished by adding to 2 mg/mL of GH in PBS pH 7.0, 5 mM of Me-PEG aldehyde-5000 (molecular weight 5000 daltons) and 20 mM of NaCNBH3 and gently mixing at room temperature for 3 hours. Ethanolamine is then added to 50 mM to reductively amidate the remaining unreacted Me-PEG. The mixture is separated on an anion-exchange column, FPLC Mono Q. The surplus unreacted Me-PEG does not bind to the column and can then be separated from the mixture. Two main PEGylated GH fractions are obtained with apparent molecular weights of 30K and 40K on reduced SDS-PAGE, vs. 20K of the unreacted GH. GH-GHBP complex is PEGylated in the same manner to give a derivative of 150K by gel filtration.

PEGylation with N-hydroxysuccinimidyl PEG (NHS-PEG) and purification are accomplished by adding NHS-PEG at a 5-fold molar excess of the total lysine concentration of GH to a solution containing 2 mg/mL of GH in 50 mM of sodium borate buffer at pH 8.5 or PBS at pH 7, and mixing at room temperature for one hour. Products are separated on a Superose 12 sizing column and/or Mono Q of FPLC. The PEGylated GH varies in size depending on the pH of the reaction from approximately 300 K for the reaction run at pH 8.5 to 40 K for pH 7.0 as measured by gel filtration. The GH-GHBP complex is also PEGylated the same way with a resulting molecular weight of 400 to 600 Kd from gel filtration.

PEGylation of the cysteine mutants of GH with PEG-maleimide is accomplished by preparing a single cysteine mutant of GH by site-directed mutagenesis, secreting it from an *E. coli* 16C9 strain (W3110 delta tonA phoA delta E15 delta (argF-lac) 169 deoC2 that does not produce the deoC protein and is described in U.S. Ser. No. 07/224,520 filed Jul. 26, 1988, now abandoned, the disclosure of which is incorporated herein by reference) and purifying it on an anion-exchange column. PEG-maleimide is made by reacting monomethoxyPEG amine with sulfo-MBs in 0.1 M sodium phosphate pH 7.5 for one hour at room temperature and buffer exchanged to phosphate buffer pH 6.2. Next GH with a free extra cysteine is mixed in for one hour and the final mixture is separated on a Mono Q column as in Me-PEG aldehyde PEGylated GH.

As ester bonds are chemically and physiologically labile, it may be preferable to use a PEG reagent in the conjugating reaction that does not contain ester functionality. For example, a carbamate linkage can be made by reacting PEG-monomethyl ether with phosgene to give the PEG-chloroformate. This reagent could then be used in the same manner as the NHS ester to functionalize lysine side-chain amines. In another example, a urea linkage is made by reacting an amino-PEG-monomethyl ether with phosgene. This would produce a PEG-isocyanate that will react with lysine amines.

A preferred manner of making PEG-GH, which does not contain a cleavable ester in the PEG reagent, is described as follows: Methoxypoly(ethylene glycol) is converted to a carboxylic acid by titration with sodium naphthalene to generate the alkoxide, followed by treatment with bromo-ethyl acetate to form the ethyl ester, followed by hydrolysis to the corresponding carboxylic acid by treatment with sodium hydroxide and water, as reported by Bückmann et al., *Macromol. Chem.*, 182:1379–1384 (1981). The resultant carboxylic acid is then converted to a PEG-N-hydroxysuccinimidyl ester suitable for acylation of GH by reaction of the resultant carboxylic acid with dicyclohexylcarbodiimide and NHS in ethyl acetate.

The resultant NHS-PEG reagent is then reacted with 12 mg/mL of GH using a 30-fold molar excess over GH in a sodium borate buffer, pH 8.5, at room temperature for one hour and applied to a Q Sepharose column in Tris buffer and eluted with a salt gradient. Then it is applied to a second column (phenyl Toyopearl) equilibrated in 0.3 M sodium citrate buffer, pH 7.8. The PEGylated GH is then eluted with a reverse salt gradient, pooled, and buffer-exchanged using a G25 desalting column into a mannitol, glycine, and sodium phosphate buffer at pH 7.4 to obtain a suitable formulated PEG7-GH.

The PEGylated GH molecules and GH-GHBP complex can be characterized by SDS-PAGE, gel filtration, NMR, tryptic mapping, liquid chromatography-mass spectrophotometry, and in vitro biological assay. The extent of PEGylation is suitably first shown by SDS-PAGE and gel filtration and then analyzed by NMR, which has a specific resonance peak for the methylene hydrogens of PEG. The number of PEG groups on each molecule can be calculated from the NMR spectrum or mass spectrometry. Polyacrylamide gel electrophoresis in 10% SDS is appropriately run in 10 mM Tris-HCl pH 8.0, 100 mM NaCl as elution buffer. To demonstrate which residue is PEGylated, tryptic mapping can be performed. Thus, PEGylated GH is digested with trypsin at the protein/enzyme ratio of 100 to 1 in mg basis at 37° C. for 4 hours in 100 mM sodium acetate, 10 mM Tris-HCl, 1 mM calcium chloride, pH 8.3, and acidified to pH<4 to stop digestion before separating on HPLC Nucleosil C-18 (4.6 mm×150 mm, 5µ, 100A). The chromatogram is compared to that of non-PEGylated starting material. Each peak can then be analyzed by mass spectrometry to verify the size of the fragment in the peak. The fragment(s) that carried PEG groups are usually not retained on the HPLC column after injection and disappear from the chromatograph. Such disappearance from the chromatograph is an indication of PEGylation on that particular fragment that should contain at least one lysine residue. PEGylated GH may then be assayed for its ability to bind to the GHBP by conventional methods.

The various PEGylation methods used produced various kinds of PEGylated wild-type GH, with apparent molecular weights of 35K, 51K, 250K, and 300K by size exclusion chromatography, which should be close to their native hydrodynamic volume. These were designated PEG1-GH, PEG2-GH, PEG3-GH, and PEG7-GH, respectively. From the results of the tryptic mapping, the PEG1-GH and PEG2-GH both had the N-terminal 9-amino-acid fragment missing from the chromatogram and possibly PEGylated, which could be confirmed by the mass spectrometry of the big molecular species found in the flow-through of the liquid chromatograph. From the molecular weight on SDS-PAGE, PEG1-GH may have one PEG on the N-terminal amine, and the PEG2-GH may have two PEG molecules on the N-terminal amine, forming a tertiary amide. The PEG3-GH has about 5 PEG groups per molecule based upon the NMR result, and on the tryptic map, at least five peptide fragments were missing, suggesting that they are PEGylated. The PEG7-GH molecule is believed to have 6–7 PEG groups per molecule based on mass spectrometry.

The sites for adding PEG groups to GH, and those that are preferred residues for such conjugation, are N-terminal methionine or phenylalanine, lysine 38, lysine 41, lysine 70, lysine 140, lysine 145, lysine 158, and lysine 168. Two lysines that appeared not to be PEGylated were lysine 115 and lysine 172.

The GH to be used for in vivo administration must be sterile. This is readily accomplished by filtration through sterile filtration membranes, prior to or following lyophilization and reconstitution. The GH ordinarily will be stored in lyophilized form or in solution.

Therapeutic GH compositions generally are placed into a container having a sterile access port, for example, an intravenous solution bag or vial having a stopper pierceable by a hypodermic injection needle.

The route of GH administration is in accord with known methods. Examples of parenteral administration include subcutaneous, intramuscular, intravenous, intraarterial, and intraperitoneal administration, or by sustained release systems as noted below. Subcutaneous and intravenous injection or infusion is preferred.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al., Biopolymers 22:547–556 [1983]), poly(2-hydroxyethyl-methacrylate) (Langer et al., J. Biomed. Mater. Res. 15:167–277 [1981] and Langer, Chem. Tech. 12:98–105 [1982]), ethylene vinyl acetate (Langer et al., supra) or poly-D-(−)-3-hydroxybutyric acid (EP 133,988). Sustained-release GH compositions also include liposomally entrapped GH. Liposomes containing GH are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamelar type in which the lipid content is greater than about 30 mol. % cholesterol, the selected proportion being adjusted for the optimal GH therapy.

An "effective amount" of GH to be employed therapeutically will depend, for example, upon the route of administration, and the condition of the patient. Accordingly, it will be necessary for the therapist to titer the dosage and modify the route of administration as required to obtain the optimal therapeutic effect. Typically, the clinician will administer the GH until a dosage is reached that achieves the desired effect. The progress of this therapy is easily monitored by conventional assays.

In the treatment of congestive heart failure by GH, the GH composition will be formulated, dosed, and administered in a fashion consistent with good medical practice. Factors for consideration in this context include the particular mammal being treated, the clinical condition of the individual patient, the site of delivery of the GH, the particular type of GH, the method of administration, the scheduling of administration, and other factors known to medical practitioners. The "therapeutically effective amount" of GH to be administered will be governed by such considerations, and is the minimum amount necessary to ameliorate, or treat the congestive heart failure, so as to increase ventricular contractility and decrease peripheral vascular resistance, or to ameliorate other conditions of similar importance in congestive heart failure patients. Such amount is preferably below the amount that is toxic to the host or renders the host significantly more susceptible to infections.

As a general proposition, the total pharmaceutically effective amount of GH administered parenterally per dose will be in the range of about 1 µg/kg/day to 10 mg/kg/day of patient body weight, although, as noted above, this will be subject to a great deal of therapeutic discretion. More preferably, this dose is at least 0.01 mg/kg/day, and most preferably for humans between about 0.01 and 1 mg/kg/day. If given continuously, the GH is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. Preferably, in human patients, a pharmaceutically effective amount of the GH administered parenterally per dose will be in the range of about 10 to 100 micrograms per kilogram of patient body weight per day.

It is noted that practitioners devising doses of both IGF-I and GH should take into account the known side effects of treatment with this hormones.

As noted above, however, these suggested amounts of GH are subject to a great deal of therapeutic discretion. The key factor in selecting an appropriate dose and scheduling is the result obtained, as indicated above.

EXAMPLES

Use of GH to Treat Congestive Heart Failure

Introduction

The goal of this study was to examine the cardiac effects of human GH treatment in an animal model of congestive heart failure.

Methods

Male Sprague-Dawley (SD) rats (Charles River Breeding Laboratories, Inc., eight weeks of age) were acclimated to the facility for at least 1 week before surgery. Rats were fed a pelleted rat chow and water ad libitum and housed in a light and temperature controlled room.

Coronary Arterial Ligation

Myocardial infarction was produced by left coronary arterial ligation as described previously. Greenen, D. L. et al., *J. Appl. Physiol.* 63:92–96 (1987); Buttrick, P. et al., *Am. J. Physiol.* 260:11473–11479 (1991). The rats were anesthetized with sodium pentobarbital (60) mg/kg, ip), intubated via tracheotomy, and ventilated by a respirator (Harvard Apparatus Model 683). After a left-sided thoracotomy, the left coronary artery was ligated approximately 2 mm from its origin with a 7-0 silk suture. Sham animals underwent the same procedure except that the suture was passed under the coronary artery and then removed. All rats were handled according to the "Position of the American Heart Association on Research Animal Use" adopted Nov. 11, 1984 by the American Heart Association. 4–6 weeks after ligation myocardial infarction could develop heart failure in rats. In clinical patients, myocardial infarction or coronary artery disease is the most common cause of heart failure. Congestive heart failure in this model reasonably mimics congestive heart failure in most human patients.

Electrocardiograms

One week after surgery, electrocardiograms were obtained under light metofane anesthesia to document the development of infarcts. The ligated rats of this study were subgrouped according to the depth and persistence of pathological Q waves across the precordial leads Buttrick, P. et al., *Am. J. Physiol.* 260:11473–11479 (1991); Kloner, R. A. et al., *Am Heart J.* 51:1009–1013 (1983). This provided a gross estimate of infarct size and assured that large and small infarcts were not differently distributed in the ligated rats treated with GH and vehicle. Confirmation was made by precise infarct size measurement.

GH Administration

Four weeks after surgery, recombinant human GH (1 mg/kg twice a day for 15 days) (Genentech, Inc., South San Francisco, Calif.) or saline vehicle was injected subcutaneously in both ligated rats and sham controls. Previous studies have shown that this dose of human GH can produce significant anabolic effects in rats. Moore et al., *Endocrinology* 122:2920–2926 (1988); R. Clark and M. Cronin, U.S. Pat. No. 5,126,324 (1992). Body weight (BW) was measured twice a week during the treatment. See FIG. 1. GH can be administered in saline or water as vehicles.

Catheterization

After 13 day treatment of GH or vehicle, rats were anesthetized with pentobarbital sodium (50 mg/kg, intraperitoneal). A catheter (PE-10 fused with PE 50) filled with heparin-saline solution (50/U/ml) was implanted into the abdominal aorta through the right femoral artery for measurement of arterial pressure and heart rate. A second catheter (PE 50) was implanted into the right atrium through the right jugular vein for measurement of right atrial pressure and for saline injection. For measurement of left ventricular pressures and contractility (dP/dt), a third catheter (PE 50) was implanted into the left ventricle through the right carotid artery. For the measurement of cardiac output by a thermodilution method, a thermistor catheter (Lyons Medical Instrument Co., Sylmar, Calif.) was inserted into the aortic root. The catheters were exteriorized at the back of the neck with the aid of a stainless steel wire tunneled subcutaneously and then fixed. Following catheter implantation, all rats were housed individually.

Hemodynamic Measurements

One day after catherization, the thermistor catheter was processed in a microcomputer system (Lyons Medical Instrument Co.) for cardiac output determination, and the other three catheters were connected to a Model CP-10 pressure transducer (Century Technology Company, Inglewood, Calif., USA) coupled to a Grass Model 7 polygraph (Grass Instruments, Quincy, Mass., USA). Mean arterial pressure (MAP), systolic arterial pressure (SAP), heart rate (HR), right atrial pressure (RAP), left ventricular systolic pressure (LVSP), left ventricular mean pressure (LVMP), left ventricular end-diastolic pressure (LVEDP) and left ventricular maximum (dP/dt) were measured in conscious, unrestrained rats. For measurement of cardiac output, 0.1 ml of isotonic saline at room temperature was injected as a bolus via the jugular vein catheter. The thermodilution curve was monitored by VR-16 simultrace recorders (Honeywell Co., NY) and cardiac output (CO) was digitally obtained by the microcomputer. Stroke volume (SV)=CO/HR; Cardiac index (CI)=CO/BW; Systemic vascular resistance (SVR)=MAP/CI.

After measurement of these hemodynamic parameters, 1 ml blood was collected through the arterial catheter. Serum was separated and stored at −70° C. for measurement of GH and IGF-1.

At the conclusion of the experiments, rats were anesthetized with pentobarbital sodium (60 mg/kg) and the heart was arrested in diastole with intra-atrial injection of KCI (1 M). The heart was removed, and the atria and great vessels were trimmed from the ventricle. The ventricle was weighed and fixed in 10% buffered formalin. See FIG. 1, Bottom.

All experimental procedures were approved by Genentech's Institutional Animal Care and Use Committee before initiation of the study.

Infarct Size Measurements

The right ventricular free wall was dissected from the left ventricle. The left ventricle was cut in four transverse slices from apex to base. Five micrometer sections were cut and stained with Massons' trichrome stain and mounted. The endocardial and epicardial circumferences of the infarcted and non-infarcted left ventrical were determined with a planimeter Digital Image Analyzer. The infarcted circumference and the left ventricular circumference of all four slices were summed separately for each of the epicardial and endocardial surfaces and the sums were expressed as a ratio of infarcted circumference to left ventricular circumference for each surface. These two ratios were then averaged and expressed as a percentage for infarct size.

Hormone Assays

Serum human GH was measured by a sensitive ELISA. A. Celniker (abstr) *Am. Endocrin Soc.*, A. Celniker et al., *Endocrinol. Metab.* 68(2):469 (1989); Greenen, D. L. et al., *J. Appl. Physiol.* 63:92–96 (1987). This assay does not detect rat GH. Total serum IGF-1 was measured after acid-ethanol extraction by radioimmunoassay, for example, RIA described by Furlanetto et al., *J. Clin. Invest.* 60:648–657 (1977); Bala and Bhaumick, *J. Clin. Endocrinol. and Metab.* 49:770–777 (1979); Zapf et al., *J. Clin. Invest.* 68:1321–1330 (1981); Hall et al., *J. Clin. Endo. Metab.* 48:271–278 (1979); EP 292,656, using human IGF-1 (Genentech M3-RD1) as the standard and a rabbit anti-IGF-1 polyclonal antiserum. The acceptable range was 1.25–40 ng/ml, while the intra and inter-assay variability were 5–9% and 6–15%, respectively. See FIG. 2.

Statistical Analysis

Results are expressed as mean±SEM. Two way and one way analysis of variance was performed to assess differences in parameters between groups. Significant differences were then subjected to post hoc analysis using the Newman-Keuls method. $P<0.05$ was considered significant.

Results

Figure 1B:
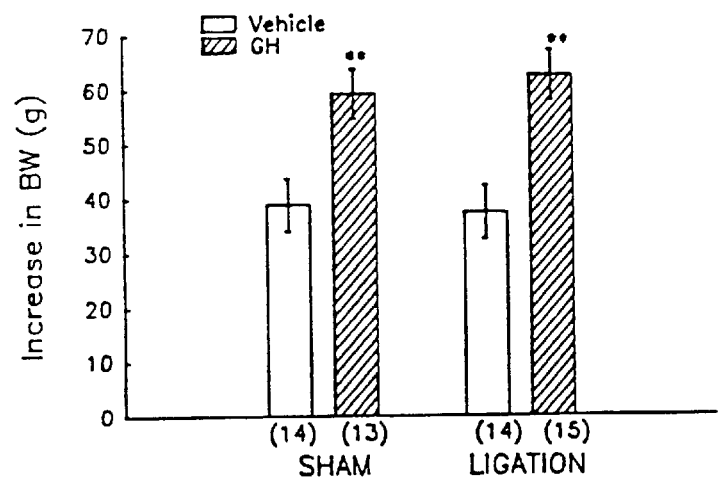
FIG. 1b. Shows an increase in body weight following treatment in ligated and sham controls. **$P<0.01$, compared to the respective vehicle group.
Figure 1C:
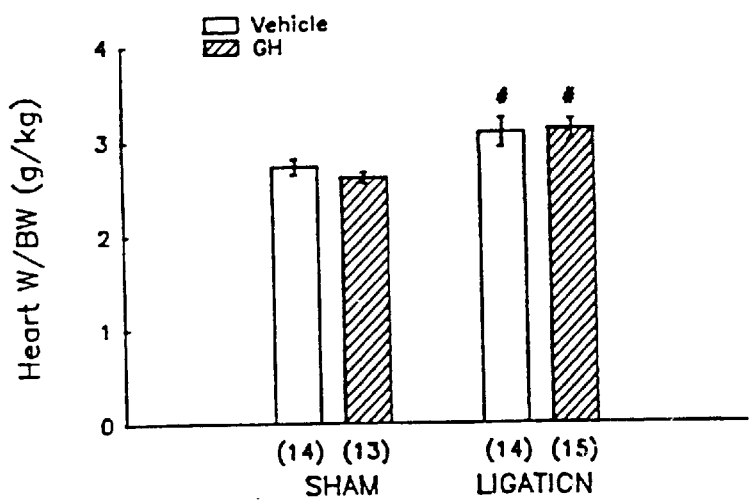
FIG. 1c. Shows a comparison of the increase in the ratio of ventricular weight to body weight in ligated and sham controls. **$P<0.01$, compared to the respective vehicle group.

The mean BW before treatment of GH or vehicle was not different between the experimental groups (FIG. 1A). There was significantly greater increase in BW following GH treatment for both sham and ligated rats (FIG. 1B). LCA ligation caused a significant increase in the ratio of ventricular weight (VW) to BW, while GH treatment did not alter this ratio significantly (FIG. 1C).

Figure 2A:
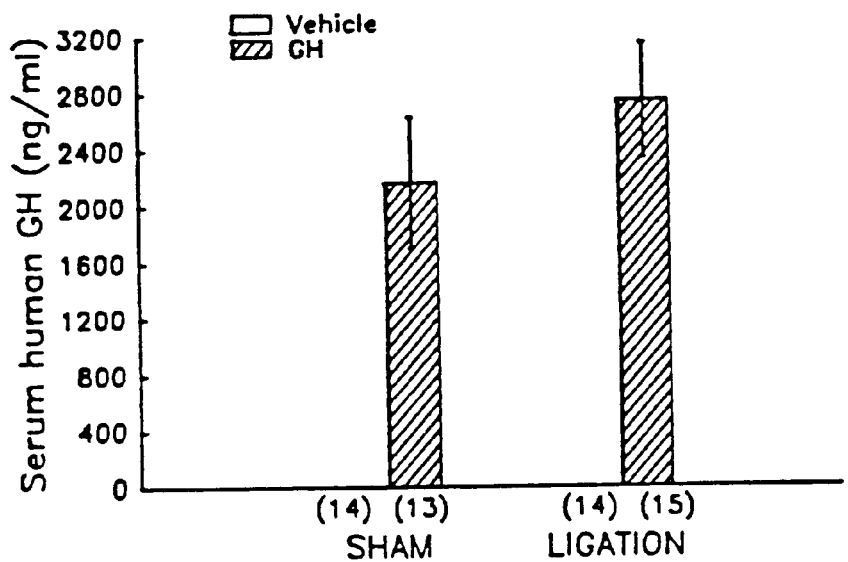
FIG. 2a. Shows the effect of GH administration on serum levels of GH in ligated and sham controls. **$P<0.01$, compared to the respective vehicle group.
Figure 2B:
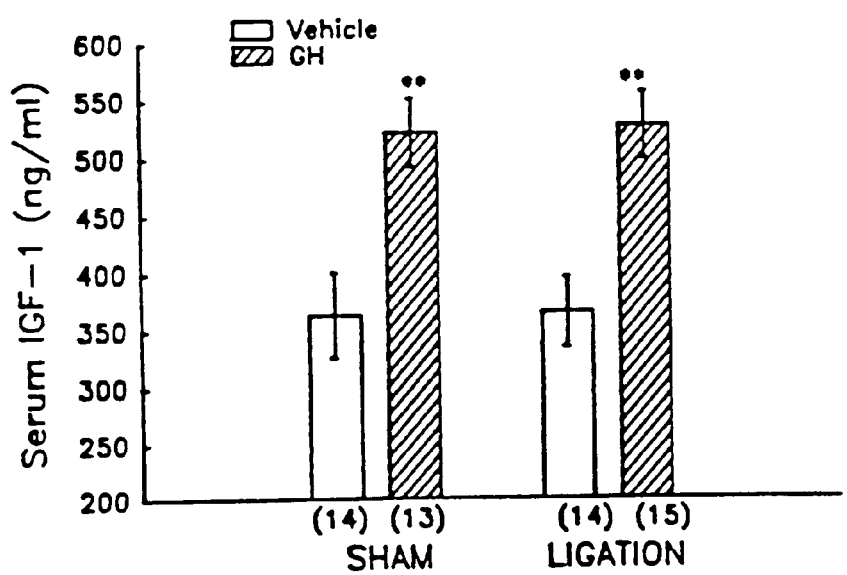
FIG. 2b. Shows the effect of GH administration on serum levels of IGF-1 in ligated and sham controls. **$P<0.01$, compared to the respective vehicle group.

GH treatment significantly increased serum levels of human GH and IGF-1 in both sham ligated rats (FIGS. 2A and 2B). The GH-induced increment in serum levels of human GH and IGF-1 was not significantly different between sham and ligated rats.

Infarct size in ligated rats was not different between the vehicle-treated group (33.2±2.2% of the left ventricle) and the GH-treated group (31.4±2.6% of the left ventricle).

Figure 3A:
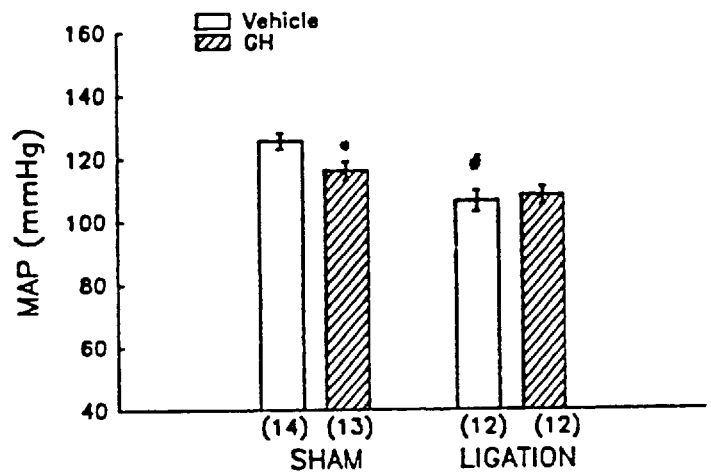
FIG. 3a. Shows the effects of GH and vehicle on mean arterial pressure (MAP) in ligated rats and sham controls. #$P<0.05$, ##$P<0.01$, compared to the respective sham group. *$P<0.05$, compared to the respective vehicle group.
Figure 3B:
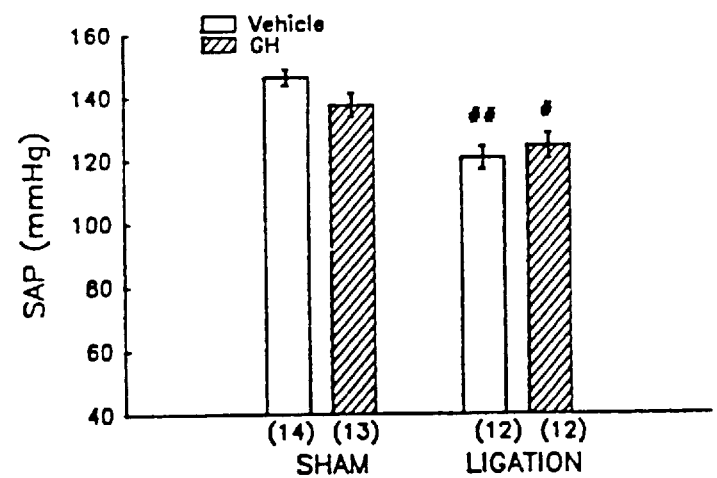
FIG. 3b. Shows the effects of GH on systolic arterial pressure (SAP) in ligated rats and sham controls. #$P<0.05$, ##$P<0.01$, compared to the respective sham group. *$P<0.05$, compared to the respective vehicle group.
Figure 3C:
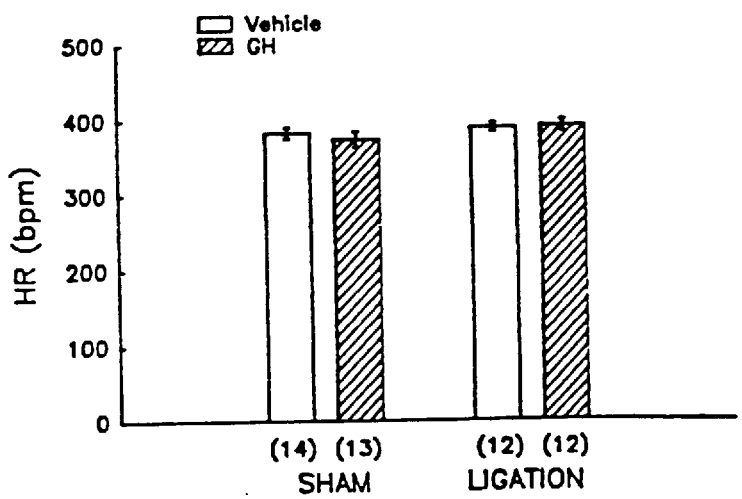
FIG. 3c. Shows the effects of GH on heart rate (HR) in ligated rats and sham controls. #$P<0.05$, ##$P<0.01$, compared to the respective sham group. *$P<0.05$, compared to the respective vehicle group.

LCA ligation resulted in significant decreases in MAP in the vehicle-treated rats but not in the GH-treated rats (FIG. 3A). GH treatment significantly decreased MAP in the sham rats but not in the ligated rats. LCA ligation was associated with significant reductions in SAP in both vehicle-treated and GH-treated rats (FIG. 3B). However, the ligation-induced decrease in SAP was significantly greater in the vehicle-treated rats than that in the GH-treated rats. GH administration did not alter SAP significantly in the sham rats. Neither LCA ligation nor GH treatment altered HR significantly (FIG. 3C).

Figure 4A:
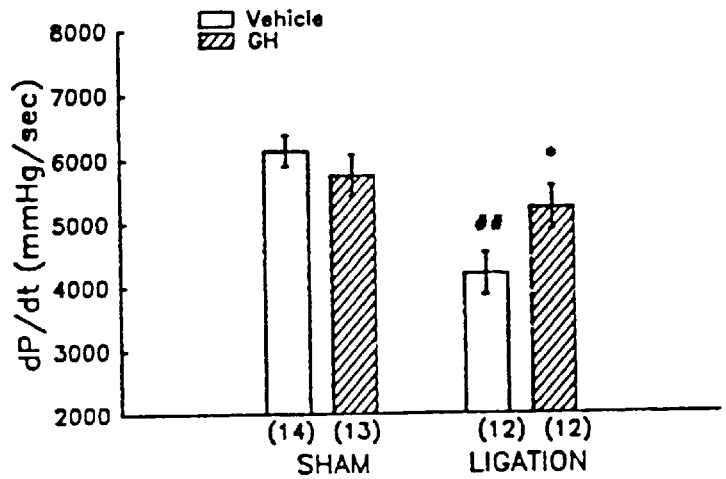
FIG. 4a. Shows the effects of GH on left ventricular maximum dP/dt. *$P<0.05$, **$P<0.01$, compared to the respective vehicle group. #P<0.05, ##P<0.01, compared to the respective sham group.
Figure 4B:
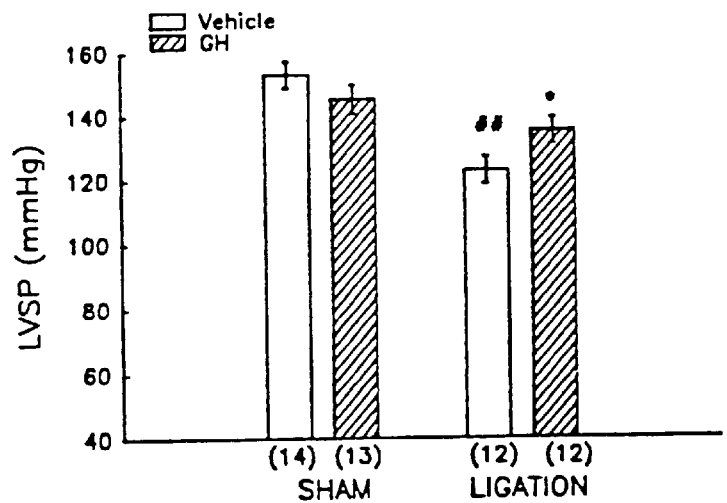
FIG. 4b. Shows the effects of growth hormone (GH) on left ventricular systolic pressure (LVSP). *P<0.05, **P<0.01, compared to the respective vehicle group. #P<0.05, ##P<0.01, compared to the respective sham group.

LCA ligation significantly lowered left ventricular dP/dt and LVSP in the vehicle-treated rats but not in the GH-treated rats (FIGS. 4A and B). GH treatment increased dP/dt and LVSP in the ligated rats but not in the sham rats.

Figure 4C:
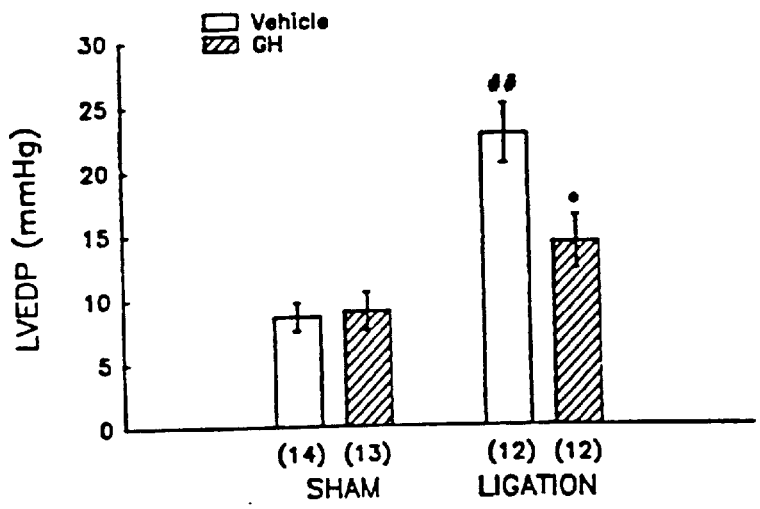
FIG. 4c. Shows the effects of growth hormone (GH) on left ventricular end-diastolic pressure (LVEDP). *P<0.05, **P<0.01, compared to the respective vehicle group. #P<0.05, ##P<0.01, compared to the respective sham group.

In the vehicle-treated animals, LVEDP was significantly elevated in the ligated group compared to sham controls (FIG. 4C). In the GH-treated animals, however, there was no significant difference in LVEDP between the ligated and sham group. GH administration decreased LVEDP significantly in the ligated rats but not in the sham rats.

Figure 5A:
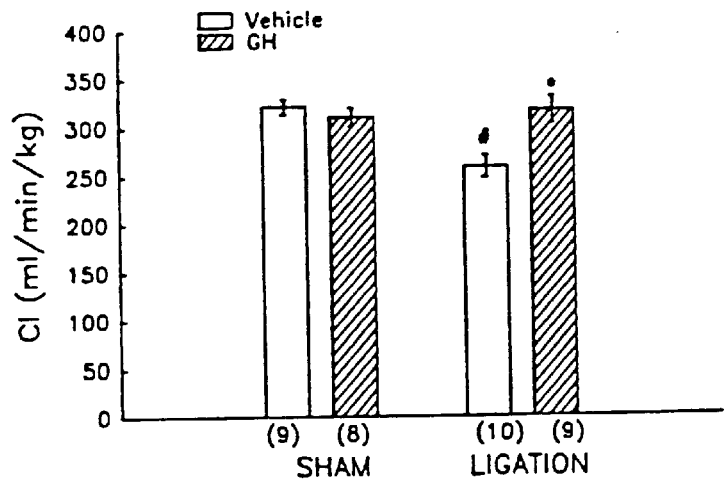
FIG. 5a. Shows the effects of growth hormone (GH) on cardiac index (CI) in ligated rats and sham controls. *P<0.05, compared to the respective vehicle group. #P<0.05, compared to the respective sham group.
Figure 5B:
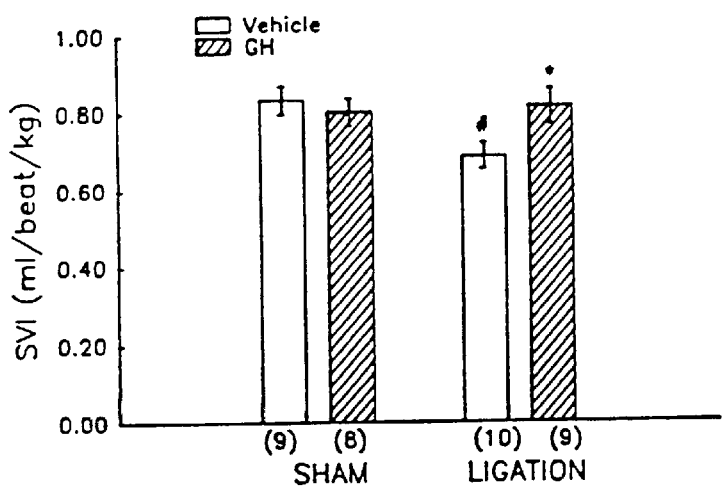
FIG. 5b. Shows the effects of growth hormone (GH) on stroke volume index, (SVI) in ligated rats and sham controls. *P<0.05, compared to the respective vehicle group. #P<0.05, compared to the respective sham group.
Figure 5C:
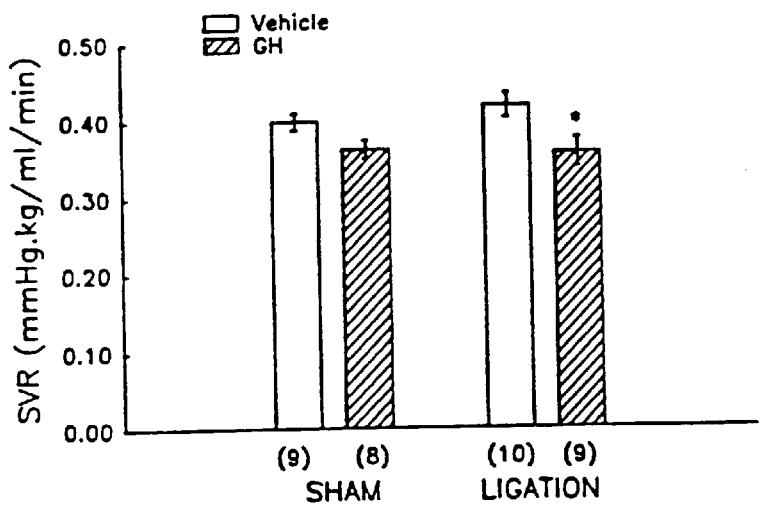
FIG. 5c. Shows the effects of growth hormone (GH) on systemic vascular resistance (SVR) in ligated rats and sham controls. *P<0.05, compared to the respective vehicle group. #P<0.05, compared to the respective sham group.

LCA ligation produced significant reductions in CI and SVI in the vehicle treated rats but not in the GH-treated rats (FIGS. 5A and B). GH administration significantly increased CI and SVI in the ligated rats but not in sham controls. There was no significant difference in SVR between the ligated and sham rats, while GH treatment significantly lowered SVR in the ligated rats and tended to lower SVR in sham controls (FIG. 5C).

In the current study, 6 weeks after left coronary artery (LCA) ligation, rats treated with vehicle exhibited significant decreases in LVSP, dP/dt, CI, and SVI and increases in LVEDP compared to the sham controls. These results indicate that congestive heart failure occurred in this animal model of myocardial infarction primarily due to a decrease in ventricular contractility. GH treatment at the dose of 2 mg/kg/day for 15 days significantly increased LVSP, dP/dt, CO, and SVI and reduced LVEDP and SVR in the LCA ligated rats. This result demonstrates that administration of GH improves cardiac function by increasing ventricular contractility and decreasing peripheral vascular resistance in congestive heart failure. In sham rats, however, GH administration at this dose did not significantly alter cardiac function except slightly lowering arterial pressure and peripheral vascular resistance.

It would be reasonably expected that the rat data herein may be extrapolated to horses, cows, humans and other mammals, correcting for the body weight of the mammal in accordance with recognized veterinary and clinical procedures. Using standard protocols and procedures, the veterinarian or clinician will be able to adjust the doses, scheduling, and mode of administration of GH and its variants to achieve maximal effects in the desired mammal being treated. Humans are believed to respond in this manner as well.

We claim:

1. A method of treating congestive heart failure in a mammal who is not a growth hormone-deficient adult, said method consisting essentially of administering to said mammal an effective amount of growth hormone (GH) or effective amounts of GH and an angiotensin-converting enzyme inhibitor.

2. The method of claim 1 wherein said growth hormone is human growth hormone.

3. The method of claim 1 wherein said mammal is human.

4. The method of claim 3 wherein said effective amount is in the range of 10–100 micrograms per kilogram of body weight per day.

5. The method of claim 3 wherein said administering is subcutaneous or intravenous.

6. The method of claim 1 wherein said congestive heart failure results from myocardial infarction.

7. The method of claim 1 wherein said growth hormone is a sustained-release preparation.

8. The method of claim 7 wherein the sustained-release preparation includes a polylactide.

9. The method of claim 1 wherein the growth hormone is complexed or bound to a polymer.

10. The method of claim 9 wherein the polymer is polyethylene polyol or polyoxyethylene polyol.

11. The method of claim 10 wherein the polyethylene polyol is polyethylene glycol.

12. The method of claim 1 wherein effective amounts of GH and an angiotensin-converting enzyme inhibitor are administered to said mammal.

* * * * *